(12) United States Patent
Watanabe et al.

(10) Patent No.: US 8,999,359 B2
(45) Date of Patent: Apr. 7, 2015

(54) COMPOSITION THAT PREVENTS DAMAGE TO TREES BY HARMFUL INSECTS AND A PREVENTION METHOD THEREOF

(75) Inventors: Kunitoshi Watanabe, Saitama (JP); Toshio Suzuki, Kumamoto (JP); Suguru Shinya, Kumamoto (JP)

(73) Assignee: Syngenta Crop Protection, Inc., Greensboro, NC (US)

( * ) Notice: Subject to any disclaimer, the term of this patent is extended or adjusted under 35 U.S.C. 154(b) by 826 days.

(21) Appl. No.: 13/214,577

(22) Filed: Aug. 22, 2011

(65) Prior Publication Data

US 2011/0296752 A1    Dec. 8, 2011

Related U.S. Application Data

(63) Continuation of application No. 10/598,616, filed as application No. PCT/JP2005/004718 on Mar. 10, 2005, now abandoned.

(30) Foreign Application Priority Data

Mar. 10, 2004   (JP) ................. 2004-066673

(51) Int. Cl.
- *A01N 51/00* (2006.01)
- *A01N 25/02* (2006.01)
- *A01G 7/06* (2006.01)
- *A01N 43/90* (2006.01)
- *A01N 47/40* (2006.01)

(52) U.S. Cl.
CPC ................ *A01N 51/00* (2013.01); *A01N 43/90* (2013.01); *A01N 47/40* (2013.01)

(58) Field of Classification Search
CPC ........ A01N 25/00; A01N 25/02; A01N 51/00
See application file for complete search history.

(56) References Cited

U.S. PATENT DOCUMENTS

| 6,063,734 A | 5/2000 | Ogura et al. |
| 6,376,487 B1 | 4/2002 | Maienfisch et al. |

FOREIGN PATENT DOCUMENTS

| EP | 0580553 A2 | 1/1994 |
| EP | 1293122 A1 | 3/2003 |
| JP | 8175914 | 7/1996 |

OTHER PUBLICATIONS

Kim Chul-Su et al: "Chemical control of sycamore lace bug, *Corythucha ciliata*(Say)"; Journal of Korean Forestry Society; vol. 89, No. 3 (Sep. 2000), English abstract only considered.
Grosman Donald M et al: "Systemic insecticide injections for control of cone and seed insects in loblolly pine seed orchards: 2 year results"; Southern Journal of Applied Forestry; vol. 26, No. 3; (Aug. 2002).
Derwent: "Solubilised formulation for injecting into wood trunk to inhibit withering of pine trees—contains e.g. insecticide, solubilising agent contg. nonionic surfactant and solvent" (1996), Abstract for JP 8175914 A published Jul. 9, 1996.
Pesticide Fact Sheet for Clothianidin (EPA issued May 30, 2003, pp. 1-19).

*Primary Examiner* — Kortney L Klinkel
(74) *Attorney, Agent, or Firm* — Brian D. McAlhaney

(57) ABSTRACT

The present invention relates to a composition comprising a neonicotinoid-based compound having a high degree of insecticidal activity, a surfactant, and an organic solvent, which is capable of demonstrating stable effects and in which the types and amounts of surfactant and organic solvent are adjusted so as to prevent chemical damage in numerous types of trees. In addition, the present invention relates to a method for preventing damage to trees by harmful insects of numerous types of trees by injecting this composition into a tree trunk and allowing the chemical to circulate within the tree body.

3 Claims, No Drawings

COMPOSITION THAT PREVENTS DAMAGE TO TREES BY HARMFUL INSECTS AND A PREVENTION METHOD THEREOF

TECHNICAL FIELD

The present invention relates to a method for preventing damage to trees by injecting into the trunk of a tree a composition that prevents damage to trees by harmful insects, and more particularly, to a method for preventing damage to trees by injecting into a trunk the composition in which the type and content of the surfactant is adjusted to a trunk injection preparation comprised of an insecticide or bactericide active ingredient and an organic solvent according to differences in aqueous solubility of the active ingredient and the type of trees.

BACKGROUND ART

Organisms that are harmful to trees that proliferate from spring through fall eat into the leaves, branches or tree body, and may impair tree growth or occasionally cause the tree to die. In addition, there are also a considerable number of harmful insects that are harmful to people, and damage is prevented or harmful insects are eradicated using various methods.

Although the method of spraying chemicals has primarily been employed in the past to prevent damage to trees by harmful organisms, in the case of scenic trees planted in parks, schools or residential areas, since this spraying has the risk of having an effect on the living environment of surrounding residents or causing chemical damage to the paint of automobiles and buildings, various restrictions have been placed on spraying.

In order to overcome these restrictions, trunk injection preparations have conventionally been used, in the case of pine trees in particular. Trunk injection preparations currently in use are targeted at pine wood nematodes, and prevent the death of pine trees by dispersing a chemical inside the tree body and eradicating pine wood nematodes that infiltrated therein. Although these active ingredients have insecticidal activity against pine wood nematodes, they are not recognized to have insecticidal effects on the Japanese pine sawyer that damages pine tree branches using pine wood nematodes as a medium.

In addition, in the case where the aqueous solubility of the active ingredient is low, proposals have been made to improve dispersivity of a chemical inside the tree body by preparing a solubilizing preparation containing a surfactant (Japanese Patent Laid-Open Publication No. Hei 8-175914). However, damage in the form of leaf discoloration and leaf fall occur in the case of injecting existing trunk injection preparations into trees other than pine trees using these technologies.

In addition, a chemical is used for cherry trees in which an organic phosphorus-based insecticide known as acephate filled into a water-soluble capsule is contained in a cartridge and then pounded into a tree trunk using a hammer and so forth to eradicate leaf-eating insects such as the fall webworm and cherry caterpillar. Since this chemical is pounded into a tree body after filling only the active ingredient into a capsule, it is thought to have problems with stability of the effects in consideration of the dispersivity of the chemical inside the tree body. In addition, since a cartridge must be pounded in for each 10 cm of the trunk circumference, and the cartridge remains inside the tree trunk, it also has the problem of placing a considerable burden on the tree.

The object of the present invention is to provide a composition that prevents damage to trees with only a small amount that solves the problems of trunk injection preparations currently in use by demonstrating efficacy on numerous types of trees and numerous harmful insects, causing no chemical damage, and containing an active ingredient that has a higher degree of insecticidal activity than organic phosphorus-based chemicals and other existing active ingredients.

As a result of extensive researches into solving these problems, the inventors of the present invention found that the blending of a neonicotinoid-based insecticide component demonstrates efficacy even in small amounts on harmful insects of numerous types of trees.

Neonicotinoid-based compounds per se are known, and thiamethoxam, for example, is used as an agricultural insecticide. However, the injection of these compounds into the trunk of a tree for the purpose of preventing damage to numerous types of trees by harmful insects has never been reported.

On the other hand, since there are some neonicotinoid-based compounds that have low solubility in water, they have poor dispersivity within a tree body even if injected into the tree body after dissolving in an organic solvent, resulting in the occurrence of problems with eradication effects on harmful insects.

In the composition of the present invention, the type and amount of surfactant are selected and adjusted to prevent damage to numerous types of trees by improving solubility in water of nicotinoid-based compounds inherently having a low level of aqueous solubility to facilitate dispersion of the compound within the tree body and demonstrate stable eradication effects.

Namely, the present invention is a method for preventing damage to trees by injecting into a tree a composition containing an insecticide or bactericide active ingredient, surfactant for which the type and amount are limited, water and/or an organic solvent, and dispersing that composition within the tree body to prevent and eradicate various harmful insects while causing no chemical damage.

There are no particular restrictions on the type of tree, and examples include not only mountain trees such as pine, cedar and cypress, but also fruit trees such as citrus, apple, pear, fig, persimmon, peach, grape, chestnut, cherry, plum, prune, loquat, oleaster and apricot trees, flowering trees such as lilac, sasanqua, camellia, althea and cherry trees, and yard trees such as oak, gardenia, devilwood and maple trees.

Examples of harmful insects include infestation insects such as gold beetles, leaf folders, caterpillars, sawflys and miters, sap-sucking insects such as aphids, coccids, and Ceroplastes rubens, hole-boring insects such as long-horned beetles, wood borers, weevils and lesser grain borers, harmful insects that cause damage by growing inside trees such as nematodes, harmful insects such as spider mites, and harmful insects that cause diseases such as mildew, black spot disease, black star disease, red star disease, rust disease, white spot disease, round spot disease, soot disease, root rot and swollen leaf disease.

Examples of insecticide or bactericide active ingredients that are effective in controlling these harmful insects include neonicotinoid-based insecticides such as thiamethoxam, acetamiprid, clotianidin, dinotefuran, thiacloprid, and imidacloprid, acaricides such as pyrimidifen, tebufenpyrad and chlorphenapyr, macrolide-based nematode-controlling agents and acaricides such as avermectin, milvemectin and nemadectin, ergosterol biosynthesis-inhibiting antimicrobials such as triflumizole, bitertanol and fenarimol, dithiocarbamate-based antimicrobials such as thiuram, zineb and mancozeb, carbendazim-producing antimicrobials such as benomyl and zetophencarb, and antibiotics such as kasugamycin, polyoxine and streptomycin. These insecticide or bactericide active ingredients may be used alone or as a combination of two or more types.

Since many of these active ingredients are hardly soluble in water, simply dissolving the active ingredient in an organic solvent does not allow the obtaining stable effects in nearly all cases due to poor dispersion within the tree body as a result of the active ingredient not being dissolved in the flow of sap through the trunk. Consequently, the use of a surfactant is an effective means for dissolving the active ingredient in the trunk flow. There are no particular restrictions on the surfactant used, and a nonionic, anionic or cationic surfactant may be used.

Examples of anionic surfactants used in the composition of the present invention include alkyl sulfate esters, alkane sulfonates, alkyl benzene sulfonates, alkyl phosphate esters, N-acyl sarcosine salts, N-acyl alanine salts and succinates, cationic surfactants such as alkyl amines, alkyl trimethyl ammonium salts, dialkyl dimethyl ammonium salts, alkyl dimethyl benzyl ammonium salts and alkyl pyridinium salts, and nonionic surfactants such as polyoxyethylene castor oils, polyoxyethylene hardened castor oils, polyoxyethylene alkyl ethers, polyoxyethylene alkyl phenyl ethers, polyoxyethylene alkyl phenyl ether formaldehyde condensation products, polyoxyethylene allyl phenyl ethers, polyoxyethylene allyl phenyl ether formaldehyde condensation products, polyethylene glycol fatty acid esters, polyoxyalkylene alkyl ethers, sorbitan fatty acid esters, polyoxyethylene sorbitan fatty acid esters, polyoxyethylene sorbitol fatty acid esters, polyglycerin fatty acid esters, sucrose fatty acid esters and propylene glycol mono fatty acid esters.

Among these, a suitable nonionic surfactant is normally used alone or as a mixture with an anionic surfactant. In addition, since there are cases where chemical damage may be caused according to the type of tree depending on the type and blended amount of surfactant, it is necessary to suitably adjust the surfactant according to the target tree type. Preferable examples of nonionic surfactants particularly include polyoxyethylene hardened castor oils, polyoxyethylene alkyl ethers, polyoxyalkylene alkyl ethers, polyoxyethylene allyl phenyl ethers and polyoxyethylene sorbitan fatty acid esters.

The solvent used in the composition of the present invention is preferably that which is easily miscible with water, examples of which include lower alcohols such as methanol and ethanol, ethers such as dioxane and tetrahydrofuran, ketones such as acetone, methyl ethyl ketone and cyclohexanone, esters such as ethyl acetate and butyl acetate, sulfoxides such as dimethyl sulfoxide, nitriles such as acetonitrile, pyrrolidones such as N-methylpyrrolidone and N-ethylpyrrolidone, amides such as N,N-dimethylformamide, and glycols such as ethylene glycol, propylene glycol and diethylene glycol, their esters and their ethers.

Since the composition may not be injected into the tree body if the viscosity is excessively high, normally a solvent having low viscosity is preferable. In addition, since these organic solvents may also cause chemical damage according to the type of tree depending on the type and blended amount in the same manner as surfactant, it is necessary to suitably adjust the solvent according to the target tree type.

Fertilizer components and trace elements and so forth that have the action of activating trees and plants can also be blended into the composition of the present invention as other components. The injection of these components into a tree body after blending into the composition is an effective method for activating trees that have been emaciated by insect damage. In addition to the three major fertilizer elements of nitrogen, phosphorus and potash, these components also include trace elements such as calcium, sulfur, zinc, copper, molybdenum, boron, iron, manganese, magnesium and various vitamins.

Although the amount of each component of the composition of the present invention may be suitably altered, an active ingredient can be contained at about 0.1 to 20% and preferably about 1 to 10%, a surfactant at about 0 to 20% and preferably about 0 to 10%, and an organic solvent at about 30-80% and preferably about 40 to 70%.

The composition of the present invention is prepared by uniformly dissolving each of these components. The preparation method consists of mixing and dissolving the entire amount using a mixer in a tank of a suitable size.

The method for applying the present composition to trees consists of drilling a hole in the tree trunk, and injecting the composition of the present invention contained in a suitable container either without applying pressure or under pressure. The amount applied is suitably adjusted according to the size of the tree, target harmful insect, degree of damage and so forth.

Although the following provides a detailed explanation of the contents of the present invention through its examples, the present invention is not limited to these examples.

EXAMPLE 1

Insecticidal Activity Tests on Various Harmful Insects

Insecticidal activity tests were conducted according to the following methods against various harmful insects for the neonicotinoid-based compound, thiamethoxam. Furthermore, tests were conducted using fenitrothion, an organic phosphorus-based compound, as a control in order to compare insecticidal activity. The test results are shown in Tables 1 to 3.

Test Methods

1. Insecticidal Activity Test on Japanese Pine Sawyer

After uniformly spraying pine feed trees with spraying solutions at prescribed concentrations using a sprayer, adult Japanese pine sawyers were used in testing to investigate the progress of their mortality and degree of infestation.

TABLE 1

Results of Chemical Insecticidal Activity Test on Adult Japanese Pine Sawyer

| Test Chemical | Spraying solution concentration (ppm) | Mortality (%) | | | Average infested area (cm2) |
|---|---|---|---|---|---|
| | | After 1 day | After 3 days | After 7 days | |
| Thiamethoxam | 40 | 100 | | | 0.3 |
| | 20 | 80 | 100 | | 0.4 |
| | 10 | 70 | 80 | 100 | 0.5 |
| | 5 | 10 | 60 | 100 | 1.8 |
| Fenitrothion | 40 | 90 | 100 | | 1.6 |
| | 20 | 20 | 70 | 100 | 2.4 |
| | 10 | 0 | 50 | 80 | 8.6 |
| | 5 | 10 | 10 | 10 | 23.3 |
| Control | | 0 | 0 | 0 | 23.8 |

2. Insecticidal Activity Test on Pine Caterpillar Larva

The mortality of pine caterpillar larva was investigated after uniformly spraying pine feed trees and pine caterpillar larva with spraying solutions at prescribed concentrations using a sprayer.

TABLE 2

Results of Chemical Insecticidal Activity
Test on Pine Caterpillar Larva

| Test Chemical | Spraying solution concentration (ppm) | Mortality (%) After 1 day | After 3 days | After 7 days |
|---|---|---|---|---|
| Thiamethoxam | 200 | 80 | 100 | |
| | 100 | 50 | 80 | 100 |
| | 50 | 20 | 60 | 80 |
| | 20 | 10 | 40 | 50 |
| Fenitrothion | 1000 | 100 | | |
| | 500 | 80 | 100 | |
| | 200 | 30 | 60 | 60 |
| | 100 | 10 | 10 | 20 |
| Control | | 0 | 0 | 0 |

3. Insecticidal Activity Test on Fall Webworm Larva

The progress of the mortality of fall webworm larva was investigated after uniformly spraying feed trees (cherry) and fall webworm larva with spraying solutions at prescribed concentrations using a sprayer.

TABLE 3

Results of Chemical Insecticidal Activity
Test on Fall Webworm Larva

| Test Chemical | Spraying solution concentration (ppm) | Mortality (%) After 1 day | After 3 days | After 7 days |
|---|---|---|---|---|
| Thiamethoxam | 300 | 80 | 100 | |
| | 200 | 30 | 90 | 100 |
| | 100 | 20 | 80 | 80 |
| | 50 | 0 | 30 | 50 |

TABLE 3-continued

Results of Chemical Insecticidal Activity
Test on Fall Webworm Larva

| Test Chemical | Spraying solution concentration (ppm) | Mortality (%) After 1 day | After 3 days | After 7 days |
|---|---|---|---|---|
| Fenitrothion | 1000 | 100 | | |
| | 500 | 80 | 100 | |
| | 200 | 30 | 60 | 70 |
| | 100 | 0 | 10 | 20 |
| Control | | 0 | 0 | 0 |

Test Results

As is clear from the test results shown in Tables 1 to 3, thiamethoxam, which is a kind of neonicotinoid-based compound, was observed to demonstrate a wide range of insecticidal activity at a lower chemical concentration than organic phosphorus-based insecticides used in the prior art for eradication of insects harmful to trees.

EXAMPLE 2

Investigation of Insecticidal Effects and Chemical Damage of Various Formulations Compositions containing 4% thiamethoxam, which is a kind of neonicotinoid-based compound, were obtained according to the formulations shown in Table 4. These compositions and compositions having as their active ingredient an organic phosphorus-based insecticide used as a comparative control were injected into cherry, pine and camellia trees followed by the collection of leaf samples roughly three months later and giving those samples to each harmful insect as food to investigate insecticidal effects. In addition, the presence of chemical damage over time was also investigated after injection. The injected amount was set at 600 ml per 1 m3 of timber volume of each tree. Those results are shown in Tables 5 to 9.

TABLE 4

Injection Preparation Formulas

| Raw Material Name | Formula No. 1 | 2 | 3 | 4 | 5 | 6 | 7 | 8 | 9 | 10 |
|---|---|---|---|---|---|---|---|---|---|---|
| Thiamethoxam bulk drug | 4.0 | 4.0 | 4.0 | 4.0 | 4.0 | 4.0 | 4.0 | 4.0 | 4.0 | |
| Organic phosphorus-based bulk drug | | | | | | | | | | 4.0 |
| Diethylene glycol | 30.0 | | | | | | | | | |
| Cyclohexanone | | 30.0 | | | 20.0 | 20.0 | 20.0 | 20.0 | 20.0 | |
| N-Methylpyrrolidone | | | 30.0 | | | | | | | |
| N,N-Dimethylformamide | | | | 30.0 | | | | | | |
| Acetone | 20.0 | 20.0 | 20.0 | 20.0 | 20.0 | 20.0 | 20.0 | 20.0 | 20.0 | 20.0 |
| Methanol | 31.0 | 31.0 | 31.0 | 31.0 | 41.0 | 41.0 | 41.0 | 41.0 | 41.0 | 41.0 |
| Water | 5.0 | 5.0 | 5.0 | 5.0 | 5.0 | 5.0 | 5.0 | 5.0 | 5.0 | 5.0 |
| NK1001) | 10.0 | 10.0 | 10.0 | 10.0 | | | | | | |
| NK1352) | | | | | 10.0 | | | 7.0 | 7.0 | 7.0 |
| NK13723) | | | | | | 10.0 | | | | |
| NK15484) | | | | | | | 10.0 | | | |
| NK41C5) | | | | | | | | 3.0 | | |
| NK41B6) | | | | | | | | | 3.0 | |
| Total | 100.0 | 100.0 | 100.0 | 100.0 | 100.0 | 100.0 | 100.0 | 100.0 | 100.0 | 100.0 |

Notes:
1)Polyoxyethylene hardened castor oil
2)Polyoxyethylene styryl phenyl ether
3)Polyoxyethylene nonyl phenyl ether
4)Polyoxyethylene oleyl ether
5)Calcium alkyl benzene sulfonate
6)Sodium alkyl benzene sulfonate

TABLE 5

Results of Insecticidal Effects Against Fall Webworm (Cherry)

| Formula No. | Mortality (%) | | | |
|---|---|---|---|---|
| | After 1 day | After 3 days | After 7 days | After 10 days |
| 1 | 30 | 100 | | |
| 2 | 30 | 90 | 100 | |
| 3 | 50 | 100 | | |
| 4 | 30 | 80 | 100 | |
| 5 | 40 | 80 | 100 | |
| 6 | 20 | 40 | 80 | 80 |
| 7 | 10 | 40 | 60 | 70 |
| 8 | 50 | 100 | | |
| 9 | 60 | 100 | | |
| 10 | 0 | 0 | 10 | 10 |

TABLE 6

Results of Insecticidal Effects Against Pine Caterpillar (Pine)

| Formula No. | Mortality (%) | | | |
|---|---|---|---|---|
| | After 1 day | After 3 days | After 7 days | After 10 days |
| 1 | 70 | 100 | | |
| 2 | 100 | | | |
| 3 | 80 | 100 | | |
| 4 | 70 | 90 | 100 | |
| 5 | 100 | | | |
| 6 | 0 | 30 | 60 | 60 |
| 7 | 30 | 80 | 80 | 80 |
| 8 | 90 | 100 | | |
| 9 | 80 | 100 | | |
| 10 | 0 | 0 | 0 | 0 |

TABLE 7

Results of Insecticidal Effects Against Japanese Pine Sawyer (Pine)

| Formula No. | Mortality (%) | | | |
|---|---|---|---|---|
| | After 1 day | After 3 days | After 7 days | After 10 days |
| 1 | 10 | 70 | 100 | |
| 2 | 0 | 50 | 100 | |
| 3 | 10 | 50 | 100 | |
| 4 | 20 | 80 | 100 | |
| 5 | 10 | 90 | 100 | |
| 6 | 0 | 40 | 50 | 60 |
| 7 | 0 | 50 | 70 | 70 |
| 8 | 0 | 100 | | |
| 9 | 10 | 90 | 100 | |
| 10 | 0 | 0 | 0 | 0 |

TABLE 8

Results of Insecticidal Effects Against Tea Tussock Moth (*Camellia*)

| Formula No. | Mortality (%) | | | |
|---|---|---|---|---|
| | After 1 day | After 3 days | After 7 days | After 10 days |
| 1 | 100 | | | |
| 2 | 90 | 100 | | |
| 3 | 100 | | | |
| 4 | 80 | 100 | | |
| 5 | 90 | 100 | | |
| 6 | 20 | 50 | 70 | 70 |
| 7 | 10 | 40 | 50 | 50 |
| 8 | 100 | | | |
| 9 | 90 | 100 | | |
| 10 | 0 | 0 | 0 | 0 |

TABLE 9

Results of Investigation of Chemical Damage

| Formula No. | Presence of Chemical Damage | | |
|---|---|---|---|
| | Cherry | Pine | *Camellia* |
| 1 | None | None | None |
| 2 | None | None | None |
| 3 | Leaf discoloration and falling leaves after 4 months | None | None |
| 4 | Leaf discoloration and falling leaves after 4 months | None | None |
| 5 | None | None | None |
| 6 | None | None | None |
| 7 | None | None | None |
| 8 | Leaf discoloration and falling leaves after 3 months | None | None |
| 9 | Leaf discoloration and falling leaves after 3 months | None | None |
| 10 | None | None | None |

Based on the test results shown in Tables 5 to 9, all of the compositions of the present invention exhibited stable control effects in comparison with the preparations of organic phosphorus-based compounds used as comparative controls. However, Formula Nos. 3, 4, 8 and 9 caused chemical damage to cherry trees. This is thought to be due to the types and amounts of organic solvents and surfactants blended into these compositions, and was determined in these series of tests. In addition, since Formulas Nos. 6 and 7 exhibited effects that were slightly inferior to the other formulas, this is thought to be due to poor dispersion of chemical within the tree body. On the basis of these findings, it was determined that there are differences in dispersion of chemical within the tree body as well as differences in stability of effects due to differences in the combination of surfactant and organic solvent, and these findings were obtained in this series of tests.

EXAMPLE 3

Effect Confirmation Test of a Mixed Preparation

Compositions were obtained that contained 4% of thiamethoxam, a kind of neonicotinoid-based compound, and 2% of emamectin benzoate, a kind of macrolide-based compound, according to the formula shown in Table 10. These compounds were injected into 100 black pine trees having chest-high diameter of 15 to 30 cm, and a control group of 100 black pine trees treated with no chemical was separately established followed by a comparison of the degree of withering caused by natural damage. Those results are shown in Table 11.

TABLE 10

Formulation of Injection Preparation

| Raw Material Name | Amount Blended (%) |
|---|---|
| Thiamethoxam bulk drug | 4.0 |
| Emamectin benzoate bulk drug | 2.0 |
| Cyclohexanone | 30.0 |
| NK135 | 10.0 |
| Water | 5.0 |
| Acetone | 20.0 |
| Methanol | 29.0 |
| Total | 100.0 |

TABLE 11

Results of Investigation of Withering

|  | Number of test trees | Number of surviving trees | Number of withered trees | Withering rate (%) |
|---|---|---|---|---|
| Injected group | 100 | 99 | 1 | 1.0 |
| Untreated group | 100 | 81 | 19 | 19.0 |

As is shown in Table 11, although the withering rate in the untreated group was 19.0%, the withering rate was only 1.0% in the group injected with the composition of the present invention, thereby demonstrating extremely high efficacy in preventing withering.

INDUSTRIAL APPLICABILITY

The present invention provides a composition that allows the obtaining of stable effects by blending a neonicotinoid-based compound having a high level of insecticidal activity, or blending surfactant and organic solvent with a neonicotinoid-based compound having a low degree of aqueous solubility, and is formulated so as to prevent chemical damage in numerous types of trees by adjusting the types and amounts of surfactant and organic solvent. In addition, the present invention provides a method for preventing damage to trees by harmful insects of numerous types of trees by injecting this composition into a tree trunk.

Harmful insects of numerous types of trees can be controlled by the present invention without having to spray chemicals. As a result, since there is no longer any scattering of chemicals or direct contact with chemicals, health impairment and detrimental effects on workers and surrounding residents can be eliminated, and concerns over contamination of the soil, rivers and oceans are not necessary, thereby enabling the present invention to make a significant contribution in terms of environmental protection as well.

What is claimed:

1. A method for controlling fall webworm on cherry trees, pine caterpillar and Japanese pine sawyer on pine trees and/or tea tussock moth on camellia trees, said method comprising injecting said trees with a formulation of thiamethoxam comprising:
    a) 4% thiamethoxam, 30% diethylene glycol, 20% acetone, 31% methanol, 5% water and 10% polyoxyethylene hardened castor oil;
    b) 4% thiamethoxam, 30% cyclohexanone, 20% acetone, 31% methanol, 5% water and 10% polyoxyethylene hardened castor oil;
    c) 4% thiamethoxam, 20% cyclohexanone, 20% acetone, 41% methanol, 5% water and 10% polyoxyethylene styryl phenyl ether;
    d) 4% thiamethoxam, 30% N-methylpyrrolidone, 20% acetone, 31% methanol, 5% water and 10% polyoxyethylene hardened castor oil;
    e) 4% thiamethoxam, 30% N,N-dimethylformamide, 20% acetone, 31% methanol, 5% water and 10% polyoxyethylene hardened castor oil;
    f) 4% thiamethoxam, 20% cyclohexanone, 20% acetone, 41% methanol, 5% water, 7% polyoxyethylene styryl phenyl ether and 3% calcium alkyl benzene sulfonate; or
    g) 4% thiamethoxam, 20% cyclohexanone, 20% acetone, 41% methanol, 5% water, 7% polyoxyethylene styryl phenyl ether and 3% sodium alkyl benzene sulfonate.

2. The method of claim 1, wherein the formulation of thiamethoxam comprises:
    a) 4% thiamethoxam, 30% diethylene glycol, 20% acetone, 31% methanol, 5% water and 10% polyoxyethylene hardened castor oil;
    b) 4% thiamethoxam, 30% cyclohexanone, 20% acetone, 31% methanol, 5% water and 10% polyoxyethylene hardened castor oil; or
    c) 4% thiamethoxam, 20% cyclohexanone, 20% acetone, 41% methanol, 5% water and 10% polyoxyethylene styryl phenyl ether.

3. A method for preventing withering of black pine trees comprising injecting said tree with a formulation of thiamethoxam and emamectin benzoate comprising 4% thiamethoxam, 2% emamectin benzoate, 30% cyclohexanone, 10% polyoxyethylene styryl phenyl ether, 5% water, 20% acetone and 29% methanol.

* * * * *